United States Patent [19]

Pelosi, Jr.

[11] 4,097,499

[45] Jun. 27, 1978

[54] 1-[5-(4-CHLOROPHENYL)FUR-FURYLAMINO]-2-PROPANOL HYDROCHLORIDE

[75] Inventor: Stanford S. Pelosi, Jr., Norwich, N.Y.

[73] Assignee: Morton-Norwich Products, Inc., Norwich, N.Y.

[21] Appl. No.: 820,548

[22] Filed: Aug. 1, 1977

[51] Int. Cl.$^2$ ............................................. C07D 307/52
[52] U.S. Cl. .................................. 260/347.7; 424/285
[58] Field of Search ...................................... 260/347.7

[56] References Cited

U.S. PATENT DOCUMENTS 3,377,359  4/1968  Boissier et al. ............... 260/347.7 X

OTHER PUBLICATIONS

Oleinik et al., Chemical Abstracts, vol. 78 (1973) 43169q.

Primary Examiner—Richard L. Raymond
Attorney, Agent, or Firm—Anthony J. Franze

[57] ABSTRACT

1-[5-(4-Chlorophenyl)furfurylamino]-2-propanol hydrochloride is useful as an anti-inflammatory agent.

1 Claim, No Drawings

1-[5-(4-CHLOROPHENYL)FURFURYLAMINO]-2-PROPANOL HYDROCHLORIDE

This invention relates to the compound 1-[5-(4-chlorophenyl)-furfurylamino]-2-propanol hydrochloride.

This compound possesses pharmacologic activity. It is particularly useful as an anti-inflammatory agent as evidenced by its ability to inhibit edema induced in rats by the administration of carrageenin. Thus, when administered at a dose of 300 mg/kg suspended in a vehicle such as aqueous methyl cellulose per os to rats receiving carrageenin, edema associated with that substance is inhibited [Winter et al., P.S.E.B.M. 111:544 (1962)].

This compound is preferably prepared in accordance with the following example:

5-(4-Chlorophenyl)furfural (42 g, 0.20 mole) was added in portions to a solution of 15 g (0.20 mole) of 1-amino-2-propanol in 200 ml of methanol with stirring at room temperature. The mixture was stirred for 0.5 hr., heated under reflux for 1.5 hr., and allowed to stand overnight. To this solution 7.6 g (0.20 mole) of sodium borohydride was added in portions over 1 hr. at 15°–20°. The solution was stirred at ambient temperature for 1 hr. and heated under reflux for 0.5 hr. The solvent was removed on a rotary evaporator, and the residual solid was partitioned between chloroform and water. The layers were separated, and the aqueous layer was extracted once with chloroform. The combined chloroform layers were dried over $MgSO_4$ and concentrated on a rotary evaporator. The residual solid was dissolved in 150 ml of absolute methanol with warming and was treated with 40 ml of methanolic HCl with cooling. Anhydrous ether (1 l.) was added, and the solid which was deposited was collected by filtration to give 30 g (50%) of 1-[5-(4-chlorophenyl)furfurylamino]-2-propanol hydrochloride. One recrystallization from $CH_3CN$ gave an analytical sample; m.p. 197°–202°.

Anal. Calcd. for $C_{14}H_{16}ClNO_2 \cdot HCl$: C, 55.64; H, 5.67; N, 4.64. Found: C, 55.99; 5.73; N, 4.66.

What is claimed is:

1. The compound 1-[5-(4-chlorophenyl)furfurylamino]-2-propanol hydrochloride.

* * * * *